United States Patent
Kim et al.

(10) Patent No.: US 12,245,851 B2
(45) Date of Patent: Mar. 11, 2025

(54) SYSTEM AND METHOD FOR NON-FACE-TO-FACE HEALTH STATUS MEASUREMENT THROUGH CAMERA-BASED VITAL SIGN DATA EXTRACTION AND ELECTRONIC QUESTIONNAIRE

(71) Applicant: TVSTORM CO., LTD., Seoul (KR)

(72) Inventors: Dae Yeol Kim, Seoul (KR); Jin Soo Kim, Guri-si (KR)

(73) Assignee: TVSTORM CO., LTD. (KR)

( * ) Notice: Subject to any disclaimer, the term of this patent is extended or adjusted under 35 U.S.C. 154(b) by 476 days.

(21) Appl. No.: 17/727,697

(22) Filed: Apr. 22, 2022

(65) Prior Publication Data

US 2022/0338757 A1  Oct. 27, 2022

(30) Foreign Application Priority Data

Apr. 23, 2021 (KR) .................. 10-2021-0053285

(51) Int. Cl.
| | | |
|---|---|---|
| *A61B 5/103* | (2006.01) | |
| *A61B 5/00* | (2006.01) | |
| *A61B 5/0205* | (2006.01) | |
| *A61B 5/024* | (2006.01) | |
| *A61B 5/08* | (2006.01) | |
| *A61B 5/1455* | (2006.01) | |

(Continued)

(52) U.S. Cl.
CPC .......... *A61B 5/1032* (2013.01); *A61B 5/0205* (2013.01); *A61B 5/02444* (2013.01);
(Continued)

(58) Field of Classification Search
CPC . A61B 5/1032; A61B 5/0205; A61B 5/02444; A61B 5/0816; A61B 5/14552;
(Continued)

(56) References Cited

U.S. PATENT DOCUMENTS 10,210,627 B1 * 2/2019 Vitsnudel ........... G06V 30/1914
10,311,334 B1 * 6/2019 Florez Choque .. G06V 10/7747
(Continued)

FOREIGN PATENT DOCUMENTS

| JP | 2020500570 A | 1/2020 |
|---|---|---|
| KR | 20060032409 A | 4/2006 |

(Continued)

OTHER PUBLICATIONS

Sanyal, "Algorithms for monitoring heart rate and respiratory rate from the video of a user's face." IEEE Journal of translational engineering in health and medicine vol. 6, pp. 1-11. 2018 (Year: 2018).*

(Continued)

*Primary Examiner* — Juan A Torres
(74) *Attorney, Agent, or Firm* — Renaissance IP Law Group LLP

(57) ABSTRACT

The present inventive concept relates to a non-face-to-face health status measurement system and method through a camera-based vital sign data extraction and an electronic questionnaire, providing a system and a method for monitoring various infectious diseases and enabling rapid response to the occurrence of diseases and infectious diseases by measuring a health status of a user in non-face-to-face through a vital sign data including heart rate, respiration rate, oxygen saturation, etc. extracted by using color information of a face image taken with a camera and results of an electronic questionnaire performed online.

10 Claims, 7 Drawing Sheets

(51) Int. Cl.
*G16H 10/20* (2018.01)
*G16H 40/67* (2018.01)
*G16H 50/30* (2018.01)

(52) U.S. Cl.
CPC ........ *A61B 5/0816* (2013.01); *A61B 5/14552* (2013.01); *A61B 5/7264* (2013.01); *A61B 5/7275* (2013.01); *G16H 10/20* (2018.01); *G16H 40/67* (2018.01); *G16H 50/30* (2018.01)

(58) Field of Classification Search
CPC ... A61B 5/7264; A61B 5/7275; A61B 5/0077; A61B 5/024; A61B 5/082; A61B 5/083; A61B 5/1176; G16H 10/20; G16H 40/67; G16H 50/30; G16H 30/40; G16H 50/20; G16H 10/60; G06V 40/16
USPC ......................................................... 382/128
See application file for complete search history.

(56) References Cited

U.S. PATENT DOCUMENTS

| | | | | |
|---|---|---|---|---|
| 2018/0220919 A1* | 8/2018 | Wershing | ............... | A61B 5/377 |
| 2019/0034704 A1* | 1/2019 | Qiu | ..................... | G06V 10/764 |
| 2020/0327309 A1* | 10/2020 | Cheng | .................... | G06N 3/084 |
| 2024/0130616 A1* | 4/2024 | van Zon | .............. | A61B 5/0017 |

FOREIGN PATENT DOCUMENTS

| KR | 20190035312 A | 4/2019 |
|---|---|---|
| KR | 102097246 B1 | 5/2020 |
| KR | 102141597 B1 | 8/2020 |
| KR | 20210025811 A | 3/2021 |

OTHER PUBLICATIONS

Negishi, "Contactless Vital Signs Measurement System Using RGB-Thermal Image Sensors and Its Clinical Screening Test on Patients with Seasonal Influenza". Sensors (Basel), Apr. 13, 2020 (Year: 2020).*

Liu, A novel method based on two cameras for accurate estimation of arterial oxygen saturation. BioMed. Eng. Online 2015, 14, 52 (Year: 2015).*

Kim, Dae Yeol et al., "Real-time Vital Signs Measurement System using Facial Image Data", Journal of Broadcast Engineering, vol. 26, Issue 2, pp. 132-142, 2021.

* cited by examiner

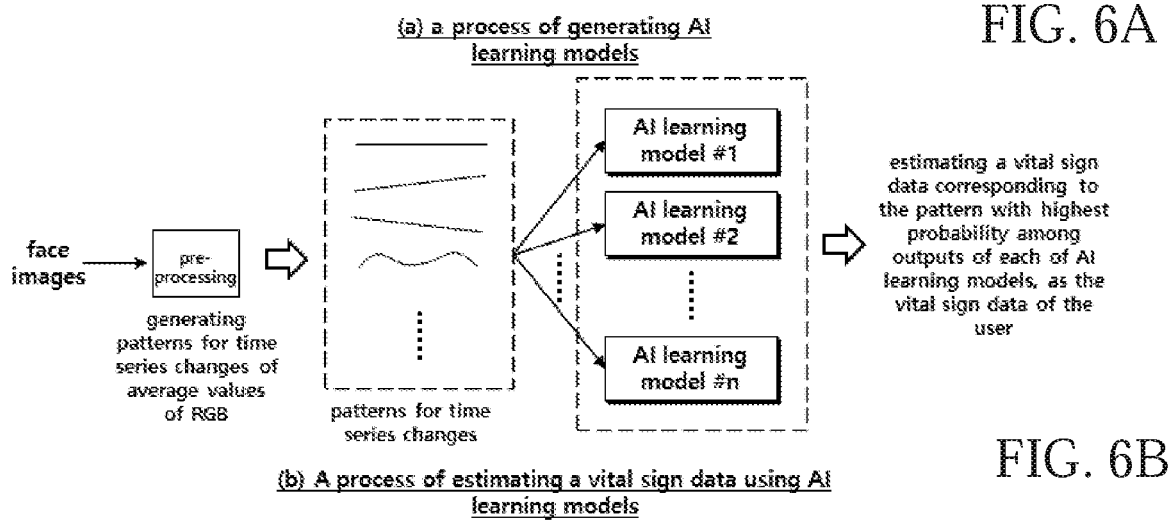
FIG. 6A
FIG. 6B
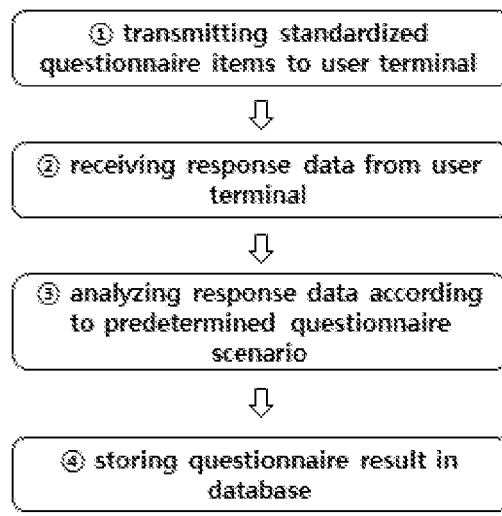
FIG. 7

SYSTEM AND METHOD FOR NON-FACE-TO-FACE HEALTH STATUS MEASUREMENT THROUGH CAMERA-BASED VITAL SIGN DATA EXTRACTION AND ELECTRONIC QUESTIONNAIRE

TECHNICAL FIELD

The present inventive disclosure relates to a non-face-to-face health status measurement system and method through a camera-based vital sign data extraction and an electronic questionnaire, in more detail, the system and method relate to measuring health status of a user in non-face-to-face through vital sign data including heart rate, respiration rate, oxygen saturation, etc. extracted by using color information of a face image taken with a camera and the results of an electronic questionnaire performed online, and thereby monitoring various infectious diseases and enabling rapid response to the occurrence of diseases and infectious diseases.

BACKGROUND ART

As infectious diseases such as corona (i.e., COVID-19) are prevalent around the world, interests in technologies for checking and deciding whether an infectious disease or an abnormality has occurred in the body is significantly ever-increasing.

People who infected with an infectious disease have different characteristics or patterns from those of ordinary people, in vital signs such as a heartbeat, a respiration, and an oxygen saturation, etc. However, it is difficult only to confirm whether an infectious disease is present or not with only a single vital sign data, but also to check important details about additional secondary infections such as contact patients and movement lines. Therefore, it is necessary to introduce a system capable of early screening for various infectious diseases and rapidly responding to secondary infections.

On the other hand, when checking whether a person has a disease, a medical staff, such as a doctor or nurse, can determine whether a patient has a disease or not by asking a patient about various matters related to the disease, in addition to the vital sign data such as heartrate, respiration rate, and oxygen saturation.

The existing representative questionnaire method is the method that a medical staff asks to a patient directly in face-to-face, in addition, there is an electronic questionnaire in which a prepared questions are asked to a patient using a smartphone or a dedicated communication terminal and then answers for the questions are received from the patient and processed. In these cases, the medical staff can perform the interview while directly accessing the past medical information of each patient that is constructed into a database.

However, if a medical staff interviews patients in face-to-face, new infectious disease patients may occur during the interview process or additional damage to the medical staff may occur. In addition, the diagnosis using the conventional questionnaire method has problems in that it is difficult to interwork with medical data, and only past historical data can be checked without checking current physical condition data of a user.

Therefore, the present inventive concept provides a method for monitoring various infectious diseases of a user and promptly responding to the spread of infection, by enabling current health status of the user to be measured non-face-to-face with only a user terminal including a smartphone without any medical equipment, through the results of the electronic questionnaire online and vital sign data such as heart rate, respiration rate, oxygen saturation, etc. extracted using color information of the face image taken with a camera.

In addition, the present inventive concept provides a method for extracting accurate and reliable vital sign data, by acquiring objective color information from the face image of the user taken by the user terminal according to the camera setting value provided from the non-face-to-face health status measurement system side to each user terminal.

Hereinafter, the prior arts existing in the technical field of the present inventive concept will be briefly described, and then the technical matters that the present inventive concept intends to achieve differently from the prior arts will be described.

First, Korean Patent Publication No. 2021-0025811 (2021 Mar. 10) relates to a health care service providing server through biometric information collection and online questionnaire, which is a prior art related to a method for providing health care service using biometric information collection and online questionnaire, wherein the prior art uses biometric information obtained from a wearable device as well as a sensor included in a smart terminal, so that it is automatically recorded without the user having to input cumbersome daily.

That is, the prior art discloses a description of a platform that helps users to improve their health habits in daily life by using biometric information such as pulse(heartrate), blood sugar, blood pressure, etc. and a questionnaire.

However, the present inventive concept is different from the technology that helps improve health habits with biometric information and questionnaire obtained from sensors or wearable devices as in the prior art, but measuring current health status of a user non-face-to-face by comprehensively referring to the vital sign data extracted using the color information of the face image taken with the camera and the result of the electronic questionnaire, and extracting vital sign data by obtaining objective color information from the face image of the user taken through each of user terminals where various camera settings are provided to each of user terminals, thus there is a significant structural difference between the prior art and the present inventive concept.

In addition, Korean Patent No. 2141597 (2020 Aug. 5) relates to a biometric information recognition device for a dog, which can acquire biometric information such as an iris or inscriptions of the dog through long-distance imaging without contact with the dog, so that it can easily obtain biometric information suitable for dog recognition and identification even from the dog that is not cooperating with humans.

That is, the prior art describes a dog biometric device that is very effective in taking images of the dog's iris or inscriptions, which induces the interest of the dog by using the face direction induction unit, causes the dog to constantly stare at the biometric device.

On the other hand, the present inventive concept does not directly obtain an image for the iris or inscription from the image as in the prior invention, but measures the user's current health status non-face-to-face only with the user terminal of the smartphone without any special medical equipment through the vital sign data extracted using the color information of the face image taken with the camera and the results of the electronic questionnaire, and extracts accurate and reliable vital sign data by obtaining objective color information from the user's face image taken through the variously set camera settings provided to each user terminal. Therefore, the difference between the prior art and the present inventive concept is clear in technical configuration.

DISCLOSURE

Technical Problem

The present inventive concept is invented to solve the above-mentioned problems, and it is an objective of the present inventive concept to provide a system and method for non-face-to-face measurement of current health status of a user only with a user terminal including a smartphone possessed by the user without any special medical equipment.

In addition, it is another objective of the present inventive concept to provide a system and method for monitoring each of various infectious diseases of a user and enabling rapid response to the spread of infection.

In addition, it is another objective of the present inventive concept to is to provide a system and method for enabling non-face-to-face measurement of health status of a user through vital sign data such as heart rate, respiration rate, oxygen saturation, etc. extracted by using color information of a face image of the user and the results of an online electronic questionnaire.

In addition, it is another objective of the present inventive concept to provide a system and method for enabling vital sign data to be extracted by obtaining objective color information from a face image of a user taken according to various camera setting values provided from the non-face-to-face health status measurement system side to each of user terminals, when vital sign data is extracted by using color information of a face image taken with a camera.

Technical Solution

A system for a non-face-to-face health status measurement through a camera-based vital sign data extraction and an electronic questionnaire according to an embodiment of the present inventive concept comprises a vital sign data extraction unit configured to extract a vital sign data from color information of a face image received from a user terminal; and an electronic questionnaire unit configured to transmit at least one or more than one of preset questionnaire items to the user terminal and receive response data for the questionnaire items from the user terminal, wherein the health status of the user is measured non-face-to-face based on the extracted vital sign data and the received response data.

In addition, the vital sign data extraction unit comprises a face image analysis engine configured to extract feature points for each of parts including eyes, nose, mouth and ears from the face image received from the user terminal, and extract at least one of regions of interest comprising a forehead, cheeks, or a combination thereof from the extracted feature points for each of the parts; and a vital sign data extraction engine configured to identify a pattern for time-series changes of average values regarding to R, G, and B of each of the extracted regions of interest, and extract the vital sign data as the vital sign data of the user, wherein the vital sign data comprises heart rate, respiration rate, oxygen saturation, or a combination thereof corresponding to the pattern with the highest degree of similarity among patterns for the identified time series change and patterns of the previously constructed mapping table.

In addition, the non-face-to-face health status measurement system further comprises a learning unit configured to construct an artificial intelligence learning model by gender, age, and race, by learning the learning data labeling a pattern for time-series changes of average values regarding to R, G, and B of a region of interest extracted from a plurality of face images and each of vital sign data for heart rate, respiration rate, and oxygen saturation corresponding to each of the patterns, wherein the vital sign data extraction engine configured to input a pattern for time-series changes of average values regarding to R, G, and B of the region of interest extracted by the face image analysis engine into each of the constructed artificial intelligence learning models, and extract the vital sign data comprising heart rate, respiration rate, oxygen saturation, or a combination thereof corresponding to the most probable pattern among the results outputted from each of the artificial intelligence learning models as the vital sign data of the user.

In addition, the non-face-to-face health status measurement system further comprises a vital sign data construction unit configured to construct a mapping table by dividing a pattern for time-series changes of average values regarding to R, G, and B of the region of interest extracted from a plurality of face images and each of the vital sign data for heart rate, respiration rate, and oxygen saturation corresponding to each of the patterns by gender, age, and race, and store the constructed mapping table in a database.

In addition, the vital sign data extraction unit is configured to provide a plurality of preset camera setting values to the user terminal and extract the vital sign data by obtaining objective color information from the face images of the user respectively taken according to the provided plurality of camera setting values, when extracting the vital sign data from the color information of the face image.

Moreover, the non-face-to-face health status measurement method through camera-based vital sign data extraction and electronic questionnaire according to an embodiment of the present inventive concept comprises extracting a vital sign data by analyzing color information of a face image received from a user terminal; and performing electronic questionnaire by transmitting preset questionnaire items to the user terminal and receiving response data for the questionnaire items from the user terminal, wherein the health status of the user is measured non-face-to-face based on the extracted vital sign data and the received response data.

In addition, extracting the vital sign data comprises extracting feature points for each of parts including eyes, nose, mouth and ears from the facial image received from the user terminal, and extracting a region of interest including a forehead, a cheek, or a combination thereof from the extracted feature points for each of the parts in a face image analysis engine of a non-face-to-face health status measurement system; and identifying a pattern for time-series changes of average values regarding to R, G, and B of the extracted region of interest, and extracting the vital sign data including heart rate, respiration rate, oxygen saturation, or a combination thereof corresponding to the pattern with the highest degree of similarity among the patterns for the identified time-series change and the patterns of the previously constructed mapping table as the vital sign data of the user, in a vital sign data extraction engine of a non-face-to-face health status measurement system.

In addition, the non-face-to-face health status measurement method further comprises learning for constructing an artificial intelligence learning model by gender, age and race by learning a learning data labeled with a pattern for time-series changes of average values regarding to R, G, and B of regions of interest extracted from a plurality of face images, and each of vital sign data for the heart rate, respiration rate, and oxygen saturation corresponding to each of the patterns, in the non-face-to-face health status measurement system; and extracting the vital sign data including heart rate, respiration rate, oxygen saturation, or a combination thereof corresponding to the most probable pattern among the results outputted from each of artificial intelligence learning models as the vital sign data of the user, after inputting the pattern for the time-series changes of average values regarding to R, G, and B of the region of interest extracted through the face image analysis engine, in the vital sign data extraction engine.

In addition, the non-face-to-face health status measurement method further comprises constructing to a mapping table by dividing the patterns for time-series changes of average values regarding to R, G, and B of the region of interest extracted from multiple face images and each of the vital sign data for heart rate, respiration rate, and oxygen saturation corresponding to each of the patterns, by gender, age, and race, and storing the constructed mapping table to a database, in a non-face-to-face health status measurement system.

In addition, the extracting of the vital sign data further comprises providing a plurality of preset camera settings values to the user terminal; and extracting the vital sign data after obtaining objective color information from each of face images of the user taken according to the plurality of the provided camera setting values, when extracting the vital sign data by analyzing the color information of the face image.

Advantageous Effects

As described above, in accordance with a non-face-to-face health status measurement system and method through camera-based vital sign data extraction and electronic questionnaire of the present inventive concept, it is effective in that the present inventive concept can improve accuracy of health status measurement for each of users, monitor various infectious diseases of each of users and quickly respond to the spread of infection, by measuring a current health status of the user by comprehensively deciding a vital sign data such as heart rate, respiration rate, and oxygen saturation extracted using color information of the face image taken with a camera and results of the online electronic questionnaire. In particular, the present inventive concept can measure a current health status of a user non-face-to-face only with a user terminal including a smart phone possessed by the user without any special medical equipment.

In addition, it is effective in that the present inventive concept provides variously set camera settings to each user terminal when extracting a vital sign data using color information of a face image taken with a camera in a non-face-to-face health status measurement system side, extracts the vital sign data by obtaining objective color information from the face image of the user captured by the user terminal according to the provided camera setting value, and thereby being able to improve the extraction accuracy and reliability of the vital sign data.

BRIEF DESCRIPTION OF THE DRAWINGS

FIGS. 6A and 6B are diagrams illustrating an example of generating an artificial intelligence learning model and estimating a vital sign data using the generated artificial intelligence learning model applied to the present inventive concept.

FIG. 7 is a detailed view showing an electronic questionnaire process according to an embodiment of the present inventive concept.

DETAILED DESCRIPTION

Figure 1:
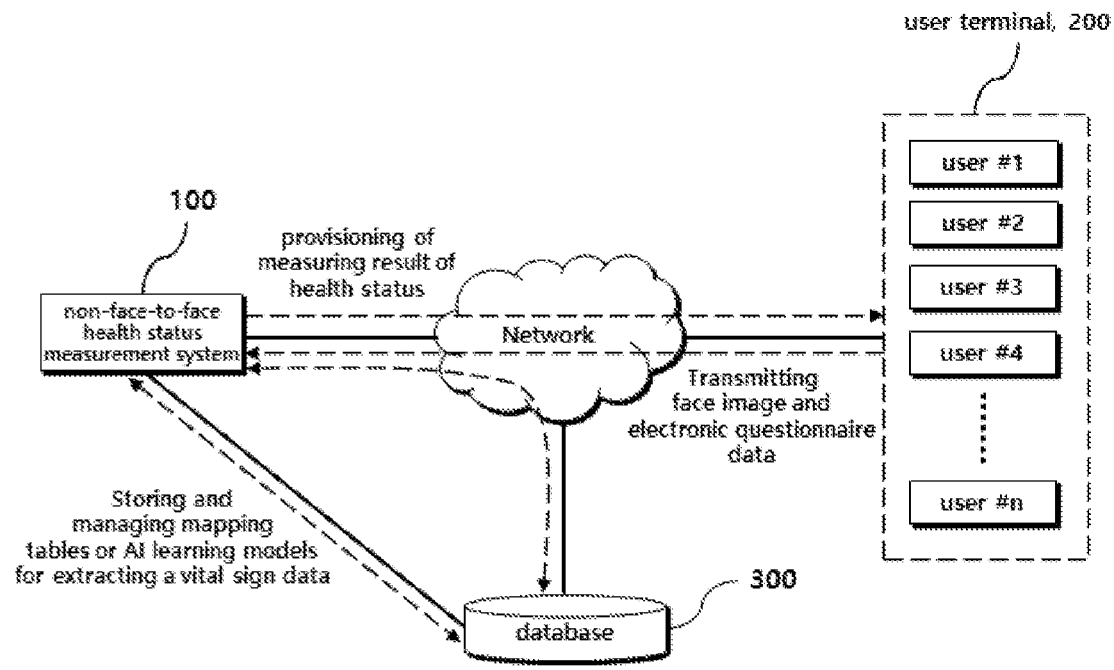
FIG. 1 is a conceptual diagram briefly illustrating a configuration of an entire environment comprising a non-face-to-face health condition measurement system through camera-based vital sign data extraction and electronic questionnaire according to an embodiment of the present inventive concept.

Hereinafter, a preferred embodiment of a non-face-to-face health condition measurement system and method through camera-based vital sign data extraction and electronic questionnaire according to the present inventive concept will be described in detail with reference to the accompanying drawings. The same reference numerals provided in each of drawings indicate the same elements. In addition, specific structural to functional descriptions for the embodiments of the present inventive concept are only exemplified for the purpose of describing the embodiments according to the present inventive concept, unless defined otherwise, all terms used herein, including technical or scientific terms, have the same meaning as commonly understood by one of ordinary skilled persons in the art to which the present inventive concept belongs. Terms such as those defined in a commonly used dictionary should be interpreted as having a meaning consistent with the meaning in the context of the related art, and unless explicitly defined herein, it is preferred not to be interpreted in an ideal or overly formal sense.

FIG. 1 is a conceptual diagram briefly illustrating a configuration of an entire environment comprising a non-face-to-face health condition measurement system through camera-based vital sign data extraction and electronic questionnaire according to an embodiment of the present inventive concept.

As shown in FIG. 1, the present inventive concept is configured to comprise a non-face-to-face health condition measurement system 100, a plurality of user terminals 200, a database 300, etc.

The non-face-to-face health status measurement system 100 provides a non-face-to-face health status measurement service that allows users to identify their current health status only with the user terminals 200 including their own smart phone, tablet PC, etc. without facing users to a medical staff or using various sensors and medical equipment.

For non-face-to-face health status measurement, the non-face-to-face health status measurement system 100 receives a face image taken with a camera from the user terminal 200, identifies the color information of R, G and B from the received face image, extracts a vital sign data including heart rate, respiration rate, oxygen saturation, etc. using the identified color information of R, G, and B. At this time, when extracting the vital sign data, it can be extracted using a mapping table or artificial intelligence learning model constructed in advance, and a detailed description thereof will be described in more detail with reference to FIG. 4 to FIG. 6 as below.

In addition, the non-face-to-face health status measurement system 100 is configured to provide a standardized questionnaire items for checking the health status to the user terminal 200 together with extracting a vital sign data, and generate an electronic questionnaire analysis result by analyzing the response data that a user inputs according to the questionnaire items.

Then, the non-face-to-face health status measurement system 100 is configured to measure a current health status of a user non-face-to-face based on the extracted vital sign data and the analyzed electronic questionnaire analysis result, and provide the measurement result to the user terminal 200.

Accordingly, the non-face-to-face health condition measurement system 100 is configured to be able to perform early screening for various infectious diseases through the health status monitoring of each user, and guide to a corresponding user to visit a medical institution immediately, when it is measured as an abnormal health status for the user, so that each user can quickly respond to an outbreak of disease or infectious disease.

The user terminal 200 is configured to be provide a camera such as a smartphone or tablet PC that a user possesses, and perform a communication connection with the non-face-to-face health condition measurement system 100 through a network, as a communication device capable of using the wired/wireless Internet. At this time, the user terminal 200 is configured to directly access to the web server of the non-face-to-face health status measurement system 100 or access to the non-face-to-face health status measurement system 100 through a dedicated application program pre-installed for non-face-to-face health condition measurement service.

In addition, the user terminal 200 is configured to transmit the face image taken by the user to the non-face-to-face health status measurement system 100 to get the non-face-to-face health status measurement service, and transmit the response data entered by the user according to the questionnaire provided by the non-face-to-face health status measurement system 100 to the non-face-to-face health status measurement system 100.

In addition, the user terminal 200 is configured to receive information about the current health status measured through the face image provided from and the electronic questionnaire performed online from the non-face-to-face health status measurement system 100, and display the information through text, graphics or a combination thereof on the screen, and thus enable the user immediately to identify the information.

The database 300 is configured to store and manage member information of each user who uses the non-face-to-face health condition measurement service, and classify, store and manage non-face-to-face health status measurement results performed by the non-face-to-face health status measurement system 100 for each user.

In addition, the database 300 is configured to store and manage a mapping table or artificial intelligence learning models used at the time when the non-face-to-face health status measurement system 100 extracts a vital sign data from color information of a face image of a user. At this time, the mapping table or artificial intelligence learning models can be provided for each gender, age, and race, respectively, and are continuously updated.

Hereinafter, the process for using such a non-face-to-face health condition measurement service is described in detail with reference to FIG. 2.

Figure 2:
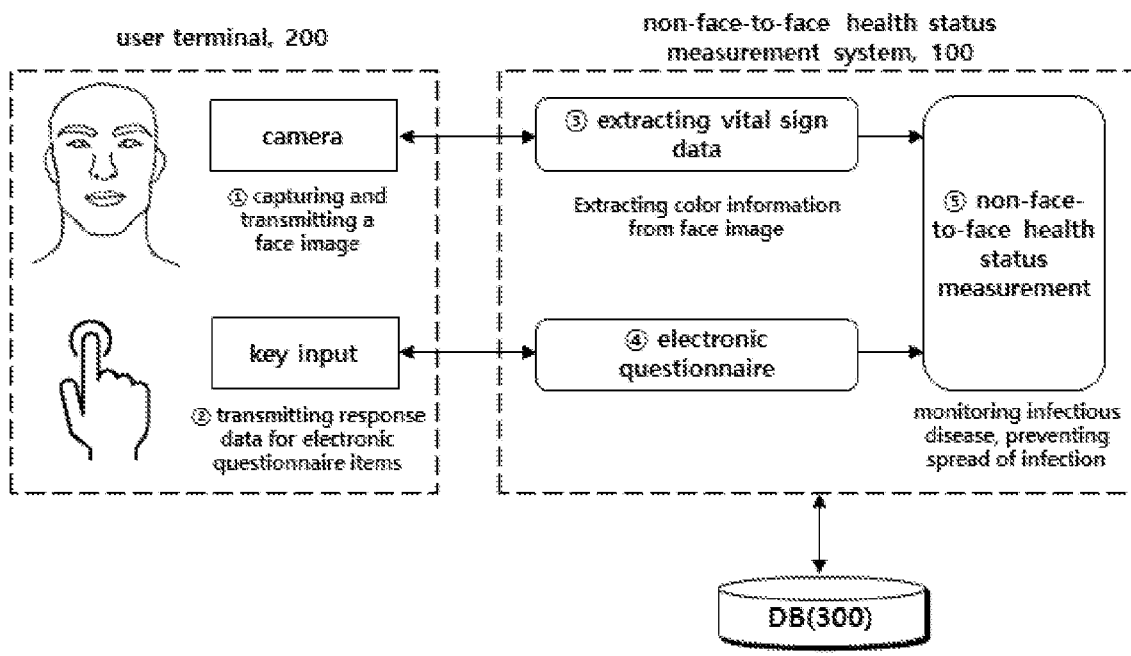
FIG. 2 is a diagram briefly illustrating an operation process of a non-face-to-face health status measurement system through camera-based vital sign data extraction and electronic questionnaire according to an embodiment of the present inventive concept.

FIG. 2 is a diagram briefly illustrating an operation process of a non-face-to-face health status measurement system through camera-based vital sign data extraction and electronic questionnaire according to an embodiment of the present inventive concept.

As shown in FIG. 2, when a specific user requests a non-face-to-face health status measurement service by performing a communication connection to the non-face-to-face health status measurement system 100 through the user terminal 200, the non-face-to-face health status measurement system 100 requests a face image of the user to the user terminal 200 and at the same time, transmits a predetermined questionnaire items to the user terminal 200 to request answers.

Accordingly, when a user takes a face image through a camera provided in a user terminal 200, the user terminal 200 transmits the face image of the user to a non-face-to-face health status measurement system 100 (①). At this time, the user can provide user information including his/her gender, age, race, or a combination thereof together with his/her face image to the non-face-to-face health status measurement system 100.

In addition, the user terminal 200 takes a face image and transmits the face image to a non-face-to-face health status measurement system 100, at the same time, the user terminal 200 transmits the response data that a user who identifies a predetermined questionnaire for the electronic questionnaire provided from the non-face-to-face health status measurement system 100 enters according to the questionnaire items, to the non-face-to-face health status measurement system 100 (②). At this time, the questionnaire items can comprise the contents of checking whether the user currently has symptoms such as fever, cough, fatigue, muscle pain, sputum headache, diarrhea, etc. and whether there is a history of infectious diseases, or a hospital visit in case of entry from abroad.

In addition, in case of receiving a face image of a user from the user terminal 200, the non-face-to-face health status measurement system 100 is configured to extract at least more than one of region of interest (ROI) from the received face image of the user, and extract a vital sign data comprising heart rate, respiration rate, oxygen saturation, etc. by analyzing the color information of R, G, and B for the extracted at least more than one region of interest (③).

In addition, the non-face-to-face health status measurement system 100 is configured to extract a vital sign data through color information analysis of a face image of a user, and then generate an electronic questionnaire analysis result through the response data to the electronic questionnaire received from the user terminal 200 (④).

Then, the non-face-to-face health status measurement system 100 is configured to be able to comprehensively identify the vital sign data comprising the extracted heart rate, respiration rate, oxygen saturation, etc. and the analyzed electronic questionnaire analysis result, and then measure the current health status of a user (⑤). That is, the non-face-to-face health status measurement system 100 is configured to identify whether a current health status of a user is normal or whether there is a need to visit a medical institution because a disease or infectious disease is predicted, through the vital sign data extracted through a facial image analysis and the online electronic questionnaire.

The result information on the health condition of a user measured in this way is provided to the user terminal 200, and thus the user can immediately identify the result information on the health status displayed on the user terminal 200. In other words, his/her own current health status can be easily identified non-face-to-face through a simple face imaging and online electronic questionnaire without having to visit a medical institution or directly meet the medical staff.

On the other hand, when the non-face-to-face health status measurement system 100 extracts a vital sign data using color information of a face image taken with a camera equipped in the user terminal 200, it can extract the vital sign data through providing variously set camera setting values to each user terminal 200 and obtains objective color information from the face image of the user taken according to the provided variously set camera setting values, in order to obtain color information objectively.

As an example, the non-face-to-face health status measurement system 100 identifies information for a camera equipped in the user terminal 200, provides the most suitable camera setting values for the user terminal 200 among a plurality of preset camera setting values, and then can extract the vital sign data by analyzing color information from a face image of the user taken according to the provided most suitable camera setting values. In addition, the non-face-to-face health status measurement system 100 provides a plurality of camera setting values to the user terminal 200, averages the color information of a face image of the user respectively taken according to the provided plurality of camera setting values, can extract the vital sign data by analyzing the averaged color information.

Figure 3:
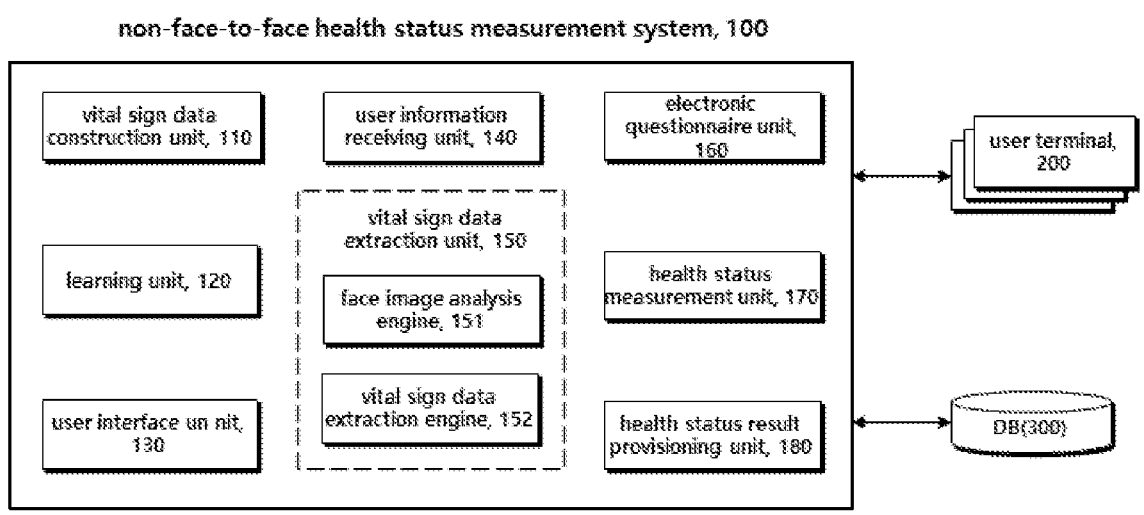
FIG. 3 is a detailed diagram illustrating a configuration of a non-face-to-face health status measurement system according to an embodiment of the present inventive concept.

FIG. 3 is a detailed diagram illustrating a configuration of a non-face-to-face health status measurement system according to an embodiment of the present inventive concept.

As shown in FIG. 3, the non-face-to-face health status measurement system 100 is configured to comprise a vital sign data construction unit 110, a learning unit 120, a user interface unit 130, a user information receiving unit 140, a vital sign data extraction unit 150, an electronic questionnaire unit 160, a health condition measurement unit 170, a health condition result provisioning unit 180, etc.

In addition, even not shown in the drawing, the non-face-to-face health status measurement system 100 is configured to further comprise a processor, a memory, a bus connecting the processor and the memory, and various interface cards, in terms of hardware, and programs to be driven through the processor are stored in the memory in terms of software, and thus further comprise an update management unit for managing updates of various operational programs, and an interface unit for transmitting and receiving data with an external device such as a database and the like.

The vital sign data construction unit 110 is configured to construct a mapping table by dividing the pattern for a time series change (e.g., change according to a time period such as 1 second, 1 minute, 10 minutes, etc.) of the average values of R, G, and B of at least one or more regions of interest extracted from face images of various people, and each vital sign data for heart rate, respiration rate, and oxygen saturation corresponding to each of the patterns, by sex(gender), age, and race, and then store the constructed mapping table in a database 300.

The learning unit 120 is configured to perform a learning of a learning data labeling a pattern for time-series changes of R, G, and B average values of regions of interest extracted from face images of various people and each of vital sign data for heart rate, respiration rate and oxygen saturation corresponding to each of the patterns, construct an artificial intelligence learning models by gender, age and race, and then store each of the constructed artificial intelligence learning models in a database 300 (Refer to FIG. 6).

On the other hand, the vital sign data constructed as a mapping table or applied to an artificial intelligence learning model is a data comprising heart rate related information (e.g. heart rate, stress index, heart rate variability, etc.), respiration rate (inhalation, exhalation)-related information, oxygen saturation, etc. measured in detail by using EIT (Electrical Impedance Tomography), a ventilator, various sensors, medical equipment, etc. at the time when various people of different gender, age, race, etc. take their own face images.

In addition, the mapping table or the artificial intelligence learning model can be managed by being periodically updated and stored in the database 300.

In addition, when the mapping table or artificial intelligence learning model is created by being classified by gender, age and race, it is possible to reduce the number of mapping tables or artificial intelligence learning models to be used for calculations through information such as gender, age, race, etc. provided by users when estimating a vital sign data from an actual face image of a user. Accordingly, there are advantages in that it is possible to not only improve the speed of estimating the vital sign data, but also reduce the system load, and the accuracy for a vital sign data extraction for each user can be improved.

In addition, it is preferable that only one of the vital sign data construction unit 110 and the learning unit 120 is applied according to an application style in the present inventive concept, but both of the styles can be used.

The user interface unit 130 is configured to transmit/receive data related to a face image, an electronic questionnaire, a health status result, etc. between a non-face-to-face health condition measurement system 100 and a user terminal 200 through a network.

The user information receiving unit 140 is configured to receive user information comprising gender, age, race, or a combination thereof of a user who performs non-face-to-face health status measurement from a user terminal 200 through the user interface unit 130 and output the received user information to the vital sign data extraction unit 150.

Figure 4:
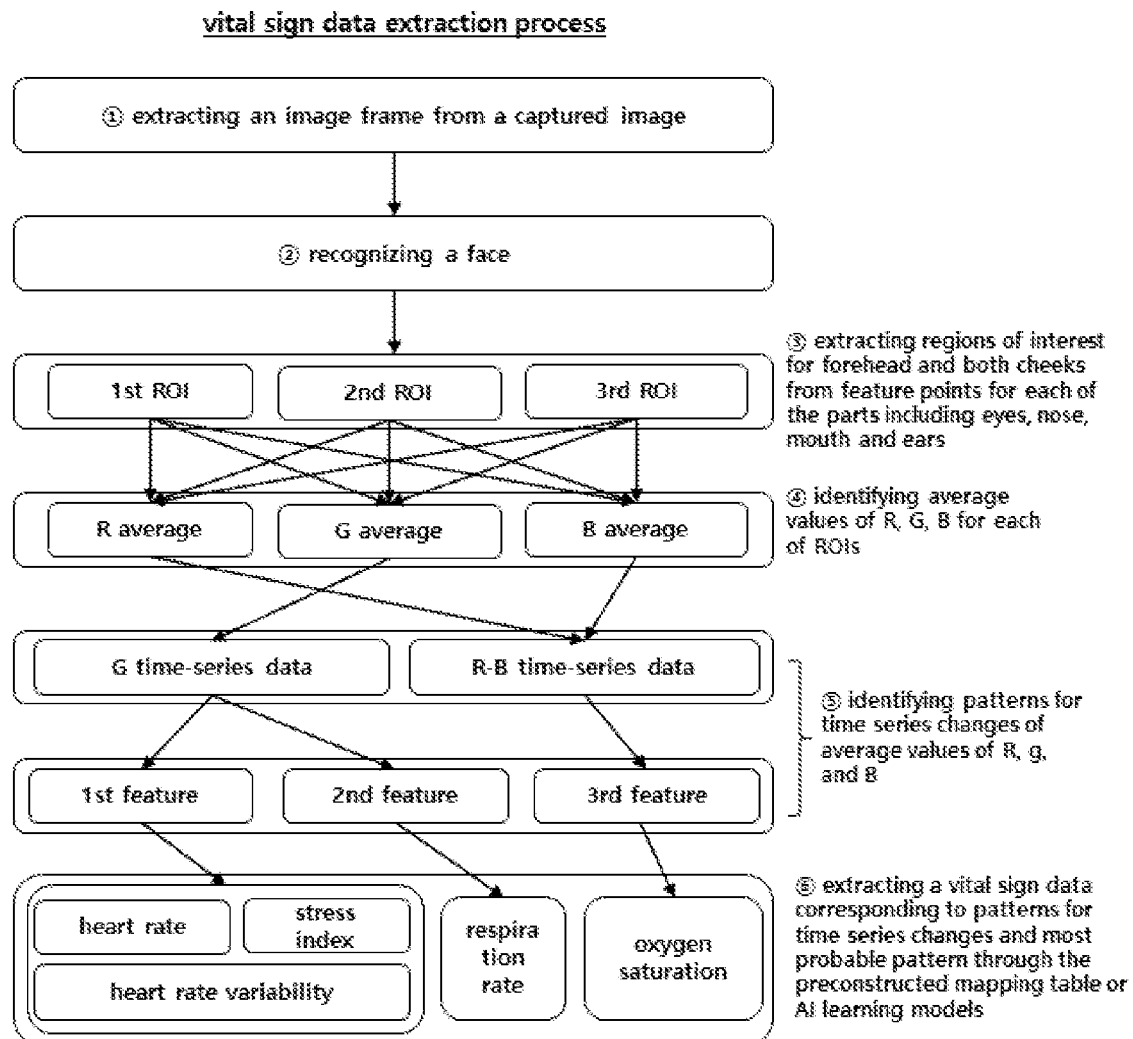
FIG. 4 is a detailed diagram illustrating a vital sign data extraction process according to an embodiment of the present inventive concept.

The vital sign data extraction unit 150 is configured to extract a vital sign data by analyzing the color information of a face image received from a user terminal 200, and output the extracted vital sign data to the health status measurement unit 170 (Refer to FIG. 4 and FIG. 5).

That is, a vital signs data comprising heart rate, respiration rate, oxygen saturation, or a combination thereof of a user is extracted with reference to the color information of a face image of the user received from the user terminal 200 through the user interface unit 130, based on the user information comprising gender, age, race, or a combination thereof of the user received from the user information receiving unit 140.

Wherein, the vital sign data extraction unit 150 comprises a face image analysis engine 151 and a vital sign data extraction engine 152.

The face image analysis engine 151 is configured to extract feature points for each of parts including eyes, nose, mouth and ears from a face image of a user received from a user terminal 200, and a region of interest including the forehead, cheeks, or a combination thereof from the extracted feature points for each of the parts.

The vital sign data extraction engine 152 is configured to obtain each of the averages for R, G, and B of the regions of interest extracted by the face image analysis engine 151, identify patterns for time series changes of the obtained R, G and B average values, compare each of the patterns of the mapping table constructed in advance through the vital sign data construction unit 110 with the identified patterns of time series changes, and extract, as a result of the comparison, the vital sign data including heart rate, respiration rate, oxygen saturation, or a combination thereof corresponding to the patterns having the highest similarity as the vital sign data of the user.

In addition, the vital sign data extraction engine 152 is configured to extract a vital sign data from a face image of a user by using artificial intelligence, beside the method that extract a vital sign data from a face image of a user by using a mapping table constructed in advance as described above.

That is, the vital sign data extraction engine 152 is configured to input patterns for time-series changes of the R, G, and B average values of regions of interest extracted by the face image analysis engine 151 into the artificial intelligence learning models constructed through the learning unit 120 by gender, age and race, and extract a vital sign data including heart rate, respiration rate, oxygen saturation, or a combination thereof corresponding to the patterns with the highest probability among results outputted from each of the artificial intelligence learning models as the vital sign data of the user.

On the other hand, when extracting a vital sign data by analyzing the color information of a face image of a user, the vital sign data extraction unit 150 is configured to provide a plurality of camera setting values set in advance to the user terminal 200, and extract the vital sign data by obtaining objective color information from the face images of the user respectively taken according to the plurality of the provided camera setting values.

The electronic questionnaire unit 160 is configured to transmit a preset medical questionnaire item to the user terminal 200, receive the response data to the questionnaire item from the user terminal 200 and output the response data to the health status measurement unit 170.

The health status measurement unit 170 is configured to identify the current health status of the user based on the vital sign data extracted from the face image of the user by the vital sign data extraction unit 150 and the response data received from the electronic questionnaire unit 160, and output information for the identified health status to the health status result provisioning unit 180. That is, the current health status of the user is measured non-face-to-face using only the face image and electronic questionnaire data to determine whether it is normal or whether there is a need to visit a medical institution (Refer to FIG. 7).

The health status result provisioning unit 180 is configured to generate health status result data by combining text, graphics or a combination thereof based on the information on the user's current health status inputted from the health status measurement unit 170, and enable the user to immediately identify the result by transmitting the generated health status result data to the corresponding user terminal 200 through the user interface unit 130.

FIG. 4 is a detailed diagram illustrating a vital sign data extraction process according to an embodiment of the present inventive concept, and FIG. 5 is a diagram for explaining an extraction of feature points for each of parts and an extraction of a region of interest according to an embodiment of the present inventive concept.

As shown in FIG. 4, the non-face-to-face health status measurement system 100 is configured to extract an image frame from a captured image (i.e., a face image) received from the user terminal 200 (①), and recognizes a face from the extracted frame (②).

Figure 5A:
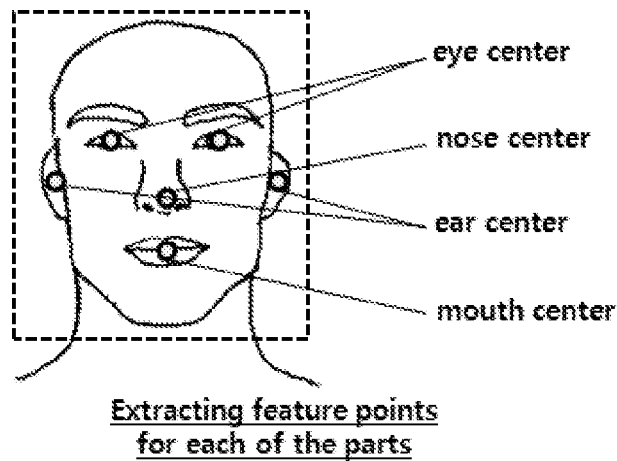
FIGS. 5A and 5B are diagrams for explaining an extraction of feature points for each of parts and an extraction of a region of interest according to an embodiment of the present inventive concept.

Next, the non-face-to-face health status measurement system 100 is configured to extract feature points for each of parts including eyes, nose, mouth and ears as shown in FIG. 5A from the recognized face area, and extract the first to third regions of interest of the forehead and both cheeks from the extracted feature points for each of the parts (③).

Figure 5B:
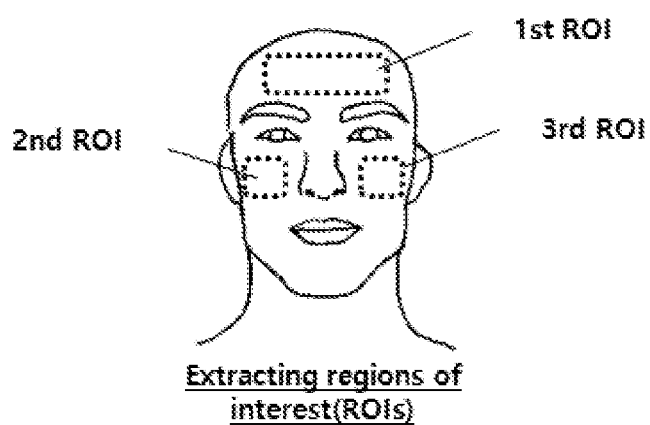

At this time, the present inventive concept, as shown in FIG. 5B, will describe the regions of interest, as examples of which three regions of interest are set including the first region of interest on the forehead and the second and third regions of interest on both cheeks. Wherein, it should be noted that the number of regions of interest can be set to less than three or more than three.

When the first to third ROIs are extracted in this way, the non-face-to-face health status measurement system 100 identifies the average values of R, G, and B for the first to third ROIs (④), classifies R, G, and B data into R-B time series data and G time series data, and identifies a first feature and a second feature indicating a pattern for the time series change of the G value, and a third feature indicating a pattern for the time series change of the R-B values (⑤).

In addition, the non-face-to-face health status measurement system 100 is configured to extract a vital sign data such as heart rate, respiration rate, oxygen saturation, etc. of the user are extracted (⑥) based on the identified first to third features by referring to information such as gender, age, race, etc. of the user who has taken a face image. That is, the vital sign data which is the most similar patterns for the time series change of the R, G, and B average values which are the first to third features or corresponding to the most probable pattern is extracted as the vital sign data of the user through the mapping table or artificial intelligence learning model constructed in advance.

As an example, heart rate-related information (e.g., heart rate, stress index, heart rate variability, etc.) can be extracted through the first feature, respiratory rate (inhalation, exhalation) related information can be extracted through the second feature, and oxygen saturation related information can be extracted through the third feature.

FIG. 6 is a diagram illustrating an example of generating an artificial intelligence learning model and estimating a vital sign data using the generated artificial intelligence learning model applied to the present inventive concept.

First, as shown in FIG. 6 (a), the non-face-to-face health status measurement system 100 is configured to create artificial intelligence learning models by gender, age and race by learning patterns for time series changes of average values of R, G, and B of the regions of interest extracted from face images of people who are different in gender, age, race, etc. and store the created artificial intelligence learning models in the database 300.

At this time, the learning data used for the learning is the data which performs labeling the vital sign data comprising heart rate, respiration rate, and oxygen saturation measured with actual medical equipment or sensors according to the patterns for time series changes of R, G, and B average values extracted from face images of various people and each of the patterns at the time the face image was taken. In addition, the pattern for the time series change can appear in a very diverse pattern which remains the same according to the unit time, gradually ascends or descends over time, repeats ascending and descending, etc.

In addition, the non-face-to-face health status measurement system 100, as shown in FIG. 6 (b), when a face image of a specific user is received from the user terminal 200, it is configured to extract feature points for each of parts of eyes, nose, mouth and ears from the face image, and extract the first to third regions of interest of the forehead and both cheeks from the extracted feature points for each of the parts. And then it is configured to perform a pre-processing for generating a pattern for time series changes of the R, G, and B average values for the first to third regions of interest.

Next, the non-face-to-face health status measurement system 100 is configured to input the patterns for time series changes of the generated R, G, and B average values to a pre-established artificial intelligence learning model for each gender, age and race, and estimate the vital sign data corresponding to the pattern with the highest probability among the results outputted from each of the artificial intelligence learning models as the vital sign data of the user who provides the face image.

FIG. 7 is a detailed view showing an electronic questionnaire process according to an embodiment of the present inventive concept.

As shown in FIG. 7, the non-face-to-face health status measurement system 100 is configured to proceed an electronic questionnaire according to the following procedure when performing the electronic questionnaire for each user who uses a non-face-to-face health status measurement service online.

More specifically, the non-face-to-face health status measurement system 100 is configured to transmit the standardized questionnaire items stored in the database 300 to the user terminal 200 that has requested the non-face-to-face health status measurement service (①).

In addition, the non-face-to-face health condition measurement system 100 is configured to receive, from the user terminal 200, the response data for each of the questionnaire items inputted by the user who has identified the standardized questionnaire items (②).

In addition, the non-face-to-face health status measurement system 100 is configured to analyze the response data for the received questionnaire item according to a predetermined questionnaire scenario to identify whether it is normal or whether the occurrence of a disease or infectious disease is predicted (③), and store the identified questionnaire result in the database 300 (④).

Accordingly, the non-face-to-face health status measurement system 100 is configured to be able to identify the current health status of the user by complexly determining the result of the electronic questionnaire and the vital sign data extracted from the face image of the user.

Hereinafter, an embodiment of the non-face-to-face health status measurement method through the camera-based vital sign data extraction and electronic questionnaire according to the present inventive concept configured as described above will be described in detail with reference to FIG. 8 and FIG. 9. Wherein, the order of each of steps according to the method of the present inventive concept can be changed by the environment of use or by a person skilled in the art.

Figure 8:
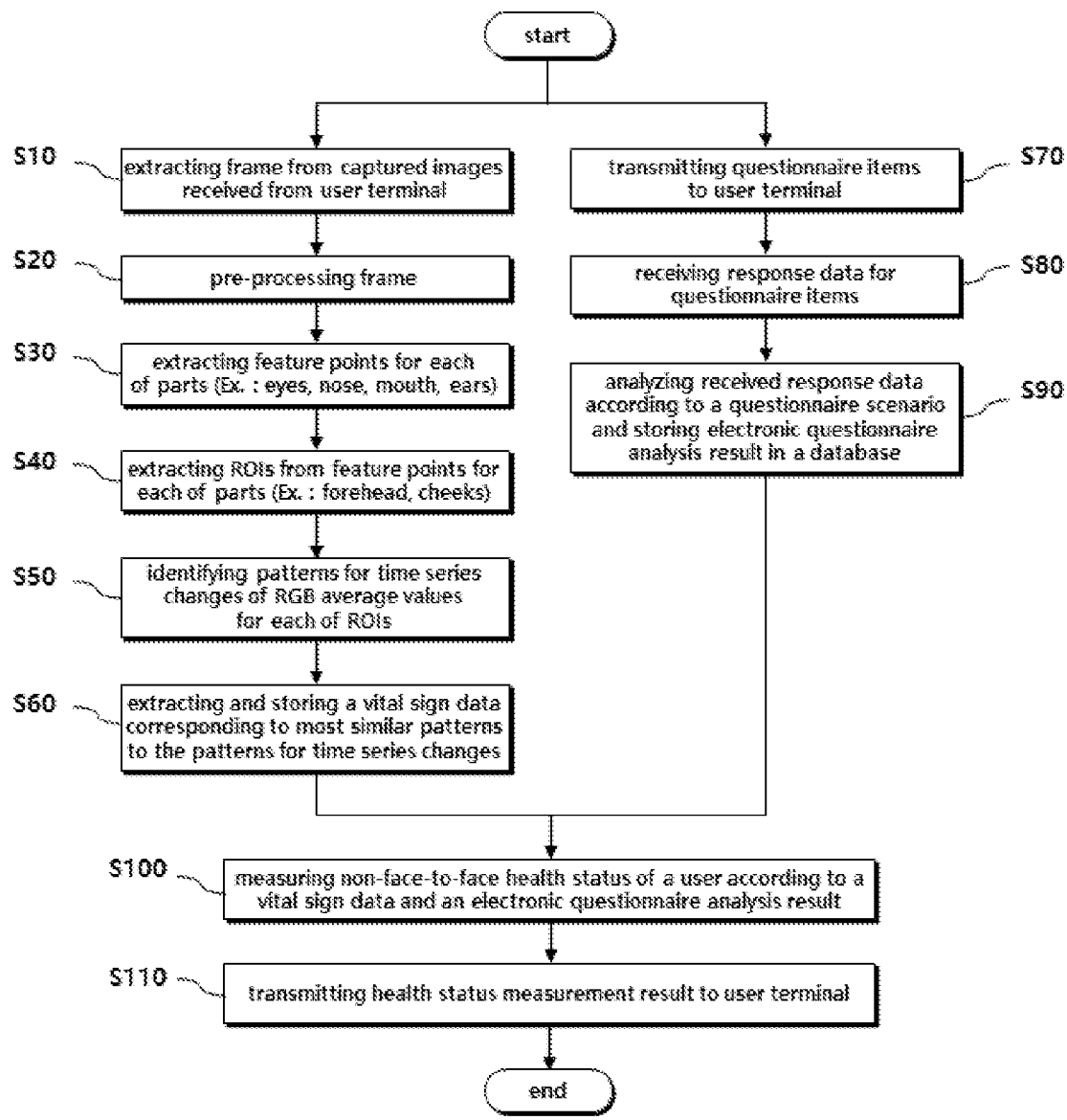
FIG. 8 is a detailed flowchart illustrating an operation process of a non-face-to-face health status measurement method through camera-based vital sign data extraction and electronic questionnaire according to an embodiment of the present inventive concept.

FIG. 8 is a detailed flowchart illustrating an operation process of a non-face-to-face health status measurement method through camera-based vital sign data extraction and electronic questionnaire according to an embodiment of the present inventive concept.

As shown in FIG. 8, the non-face-to-face health status measurement system 100 is configured to extract a frame from the captured images (i.e., face images) received from the user terminal 200 through a network S10, and pre-process the extracted frame S20. As an example, it is configured to adjust brightness, contrast, resolution, size, etc. for extracting color information from the face image.

In addition, the non-face-to-face health status measurement system 100 is configured to extract feature points for each of parts, such as eyes, nose, mouth, and ears, from the pre-processed frame S30, and extract regions of interest such as the forehead and cheeks from the extracted feature points for each of the parts S40.

Then, the non-face-to-face health status measurement system 100 is configured to identify the patterns for time series changes of the extracted R, G, and B average values for each of regions of interest S50, compare the patterns of the identified time series changes with the patterns of the mapping table constructed in advance for each gender, age and race, and extract the vital sign data including heart rate, respiration rate, oxygen saturation, or a combination thereof corresponding to the patterns with the highest similarity as the vital sign data of the user S60.

At this time, when extracting the vital sign data through the step S60 through an artificial intelligence learning model without using a mapping table constructed in advance as described above, the non-face-to-face health status measurement system 100 is configured to input the pattern of time series change of the R, G, and B average values of the region of interest identified in step S50 to the artificial intelligence learning model for each gender, age and race established in advance, and extract a vital sign data including heart rate, respiration rate, oxygen saturation, or a combination thereof corresponding to the pattern with the highest probability among the results outputted from the respective artificial intelligence learning models as the vital sign data of the user.

On the other hand, after extracting the vital sign data using the color information of the face image of the user through the steps S10 to S60, the non-face-to-face health status measurement system 100 is configured to transmit a preset questionnaire item to the user terminal 200 for an online electronic questionnaire S70.

In addition, the non-face-to-face health status measurement system 100 is configured to receive the response data for the questionnaire item from the user terminal 200 S80, generate an electronic questionnaire analysis result by analyzing the received response data according to a questionnaire scenario, and store the electronic questionnaire analysis result in the database 300 S90.

Then, the non-face-to-face health status measurement system 100 is configured to complexly decide the vital sign data extracted in the step S60 and the electronic questionnaire analysis result generated in the step S90, measure the health status of the user non-face-to-face S100, enable the user immediately identify his/her current health status S110 by transmitting the result data on the health status of the user measured through the non-face-to-face to the user terminal 200.

In addition, although not shown in the drawings, when extracting a vital sign data by analyzing the color information of the face image, the non-face-to-face health status measurement system 100 is configured to, in order to increase the objectivity of color information, provide a plurality of camera setting values set in various ways to the user terminal 200, and be able to extract, as described above, the vital sign data by obtaining color information from a face image of a user taken according to the plurality of the provided camera setting values.

Figure 9:
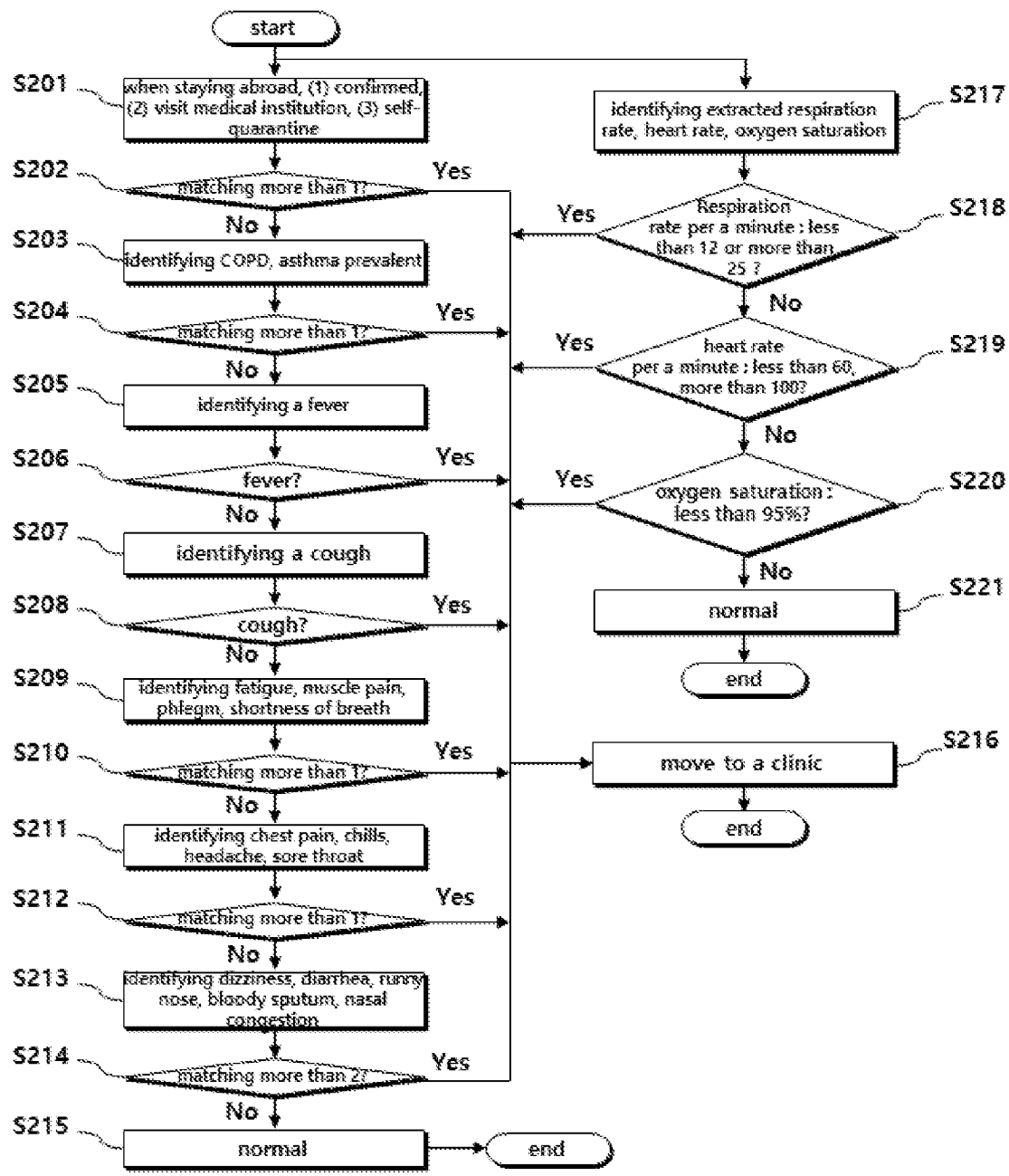
FIG. 9 is a detailed flowchart illustrating an example of a compound judgement process for an infectious disease in a non-face-to-face health status measurement system according to an embodiment of the present inventive concept.

FIG. 9 is a detailed flowchart illustrating an example of a compound judgement process for an infectious disease in a non-face-to-face health status measurement system according to an embodiment of the present inventive concept, and a detailed embodiment measuring and identifying the presence of infectious diseases by using a vital sign data extracted based on color information of face images and online electronic questionnaires non-face-to-face for users who have stayed abroad for a certain period of time.

As shown in FIG. 9, the non-face-to-face health status measurement system 100 is configured to identify three items: whether a patient having confirmed infectious disease when staying abroad, whether having a history to visit a medical institution, or whether having a history of self-quarantine S201, and determine whether at least one of the three identified items is corresponded or not S202, based on the response data to the questionnaire item received from the user terminal 200.

As a result of the determination in step S202, if more than one item is not matched, the non-face-to-face health status measurement system 100 is configured to identify whether one of COPD (chronic obstructive pulmonary disease) or asthma is prevalent or not S203, and determines whether more than one of them is corresponded or not S204.

As a result of the determination in step S204, if more than one is not matched, the non-face-to-face health status measurement system 100 is configured to identify whether a fever is present or not S205 and determine whether there is a fever symptom or not S206.

If there is no fever symptom as a result of determination in step S206, the non-face-to-face health status measurement system 100 is configured to identify whether there is a cough S207 and determine whether there is a cough symptom S208.

If there is no cough symptom as a result of determination in step S208, the non-face-to-face health status measurement system 100 is configured to identify whether there are fatigue, muscle pain, phlegm, and shortness of breath S209 and determine whether at least one of the above 4 items is corresponded S210.

As a result of the determination in step S210, if at least more than one is not matched, the non-face-to-face health status measurement system 100 is configured to identify whether there is at least one of chest pain, chills, headache, and sore throat S211 and determine whether at least more than one is matched S212.

As a result of the determination in step S212, if at least more than one is not matched, the non-face-to-face health status measurement system 100 is configured to identify whether there is at least one of dizziness, diarrhea, runny nose, bloody sputum, or nasal congestion S213 and determine whether more than two of the five are matched S214.

As a result of the determination in step S214, if more than two are not matched, the non-face-to-face health status measurement system 100 is configured to measure as normal and guide as a normal, and terminate the non-face-to-face health status measurement service S215.

However, if at least more than one item corresponds as a result of the determination in steps S202, S204, S210 and S212, if there is fever or coughing symptom as a result of the determination in steps S206 and S208, or if more than two are matched as a result of the determination in step S214, the non-face-to-face health status measurement system 100 guides movement to a clinic and terminate the non-face-to-face health status measurement service S216.

Meanwhile, the non-face-to-face health status measurement system 100 is configured to identify vital sign data including respiration rate, heart rate, and oxygen saturation extracted based on color information of the face image of the user S217.

Next, the non-face-to-face health status measurement system 100 is configured to determine whether the respiration rate identified in step S217 is less than 12 or more than 25 per a minute S218, if the respiration rate as a result of the determination is less than 12 or more than 25 per a minute, the step S216 of guiding movement to the clinic is performed and the non-face-to-face health status measurement service is terminated.

In addition, if there is no abnormality in the respiration rate as a result of the determination in step S218, the non-face-to-face health status measurement system 100 is configured to determine whether the heart rate identified in step S217 is less than 60 or greater than 100 S219, if the respiration rate is less than 60 or more than 100 as a result of the determination, the step S216 of guiding movement to the clinic is performed and the non-face-to-face health status measurement service is terminated.

In addition, if there is no abnormality in the heart rate as a result of the determination in step S219, the non-face-to-face health status measurement system 100 is configured to determine whether the oxygen saturation identified in step S217 is less than 95% S220, if the respiration rate is less than 60 or more than 100 as a result of the determination, the step S216 of guiding the movement to the clinic is performed and the non-face-to-face health status measurement service is terminated.

In addition, if there is no abnormality in oxygen saturation as a result of determining in step S220, the non-face-to-face health status measurement system 100 is configured to measure as normal and guide as normal, and the non-face-to-face health status measurement service is terminated S221.

As such, the present inventive concept provides a measurement of a current health status of a user by comprehensively determining a vital sign data extracted using color information of a face image taken with a camera and result of a electronic questionnaire, thus it is possible to increase accuracy of measuring the health status of each user, perform monitoring of various infectious diseases of each user, and be able to respond quickly to the spread of infection. In particular, the present inventive concept provides a measurement of a non-face-to-face current health status of a user only with a user terminal including a smart phone possessed by the user without any special medical equipment.

In addition, the present inventive concept can improve accuracy and reliability of extracting a vital sign data, since when extracting the vital sign data by using color information of a face image taken with a camera in the non-face-to-face health status measurement system side, various camera setting values are provided for each user terminal, and the vital sign data is extracted by obtaining objective color information from a face image of a user taken by a user terminal according to the provided camera setting values.

As described above, the present inventive concept is described with reference to the embodiments shown in the drawings, which are merely exemplary, and people who have ordinary skill in the art will understand that various modifications and equivalent other embodiments are possible therefrom. Therefore, the technical protection scope of the present inventive concept should be determined by the following claims.

What is claimed is:

1. A system for non-face-to-face health status measurement through a camera-based vital sign data extraction and an electronic questionnaire, comprising:
    a vital sign data extraction unit configured to extract a vital sign data from color information of a face image received from a user terminal, wherein the vital sign data extraction unit comprises:
        a face image analysis engine configured to extract feature points for each of parts including eyes, nose, mouth, and ears from the face image received from the user terminal, and extract regions of interest comprising a forehead, cheeks, or a combination thereof from the extracted feature points for each of the parts; and
        a vital sign data extraction engine configured to identify a pattern for time-series changes of average values regarding R, G, and B values of each of the extracted regions of interest, and extract a vital sign data as the vital sign data of the user,
        wherein the vital sign data comprises oxygen saturation corresponding to a pattern with the highest degree of similarity among patterns for an identified time series change and patterns of a previously constructed mapping table; and
    an electronic questionnaire unit configured to transmit preset questionnaire items to the user terminal and receive response data for the questionnaire items from the user terminal,
    wherein the health status of the user is measured non-face-to-face based on the extracted vital sign data and the received response data.

2. The system according to claim 1, wherein
    wherein the vital sign data further comprises heart rate, respiration rate, or a combination thereof corresponding to the pattern with the highest degree of similarity among patterns for the identified time series change and patterns of the previously constructed mapping table.

3. The system according to claim 2, further comprising:
    a learning unit configured to construct an artificial intelligence learning model by gender, age, and race, by learning the learning data labeling a pattern for time-series changes of average values regarding R, G, and B values of regions of interest extracted from a plurality of face images and each of vital sign data for heart rate, respiration rate, and oxygen saturation corresponding to each of the patterns,
    wherein the vital sign data extraction engine configured to input a pattern for time-series changes of average values regarding R, G, and B values of the regions of interest extracted by the face image analysis engine into each of the constructed artificial intelligence learning models, and extract the vital sign data comprising heart rate, respiration rate, oxygen saturation, or a combination thereof corresponding to the most probable pattern among the results outputted from each of the artificial intelligence learning models, as the vital sign data of the user.

4. The system according to claim 1, further comprising:
    a vital sign data construction unit configured to construct a mapping table by dividing a pattern for time-series changes of average values regarding R, G, and B values of the regions of interest extracted from a plurality of face images and each of the vital sign data for heart rate, respiration rate, and oxygen saturation corresponding to each of the patterns by gender, age, and race, and store the constructed mapping table in a database.

5. The system according to claim 1, wherein the vital sign data extraction unit is configured to provide a plurality of preset camera setting values to the user terminal and extract the vital sign data by obtaining objective color information from the face images of the user respectively taken according to the provided plurality of camera setting values, when extracting the vital sign data from the color information of the face image.

6. A method for a non-face-to-face health status measurement through camera-based vital sign data extraction and an electronic questionnaire, comprising:
    in a non-face-to-face health status measurement system, extracting a vital sign data from color information of a face image received from a user terminal, wherein the extracting of the vital sign data comprises:
    in a face image analysis engine of the non-face-to-face health status measurement system, extracting feature points for each of parts including eyes, nose, mouth and ears from the facial image received from the user terminal, and extracting regions of interest including a forehead, a cheek, or a combination thereof from the extracted feature points for each of the parts; and
    in a vital sign data extraction engine of the non-face-to-face health status measurement system, identifying patterns for time-series changes of average values regarding R, G, and B values of the extracted regions of interest,
    wherein the vital sign data includes oxygen saturation corresponding to a pattern with the highest degree of similarity among patterns for identified time-series changes and patterns of a previously constructed mapping table, as the vital sign data of the user; and
    in the non-face-to-face health status measurement system, performing electronic questionnaire by transmitting preset questionnaire items to the user terminal and receiving response data for the questionnaire items from the user terminal,
    wherein the health status of the user is measured non-face-to-face based on the extracted vital sign data and the received response data.

7. The method according to claim 6, wherein
    the vital sign data further includes heart rate, respiration rate, or a combination thereof corresponding to a pattern with the highest degree of similarity among the patterns for the identified time-series changes and the patterns of the previously constructed mapping table, as the vital sign data of the user.

8. The method according to claim 7, further comprising:
    in the non-face-to-face health status measurement system, learning of constructing an artificial intelligence learning model by gender, age, and race by learning a learning data labeling patterns for the time-series changes of average values regarding R, G, and B values of the regions of interest extracted from a plurality of face images, and each of vital sign data for heart rate, respiration rate, and oxygen saturation corresponding to each of the patterns; and in the vital sign data extraction engine, inputting patterns for time-series changes of average values regarding R, G, and B values of regions of interest extracted through the face image analysis engine, and extracting a vital sign data including heart rate, respiration rate, oxygen saturation, or a combination thereof corresponding to the most probable pattern among the results outputted from each of artificial intelligence learning models, as the vital sign data of the user.

9. The method according to claim 6, further comprising:
in the non-face-to-face health status measurement system, constructing a mapping table by dividing the patterns for time-series changes of average values regarding R, G, and B values of regions of interest extracted from a plurality of face images and each of the vital sign data for heart rate, respiration rate, and oxygen saturation corresponding to each of the patterns, by gender, age, and race, and storing the constructed mapping table to a database.

10. The method according to claim 6, wherein the extracting of the vital sign data further comprises:
providing a plurality of preset camera settings values to the user terminal, when extracting the vital sign data from the color information of the face image; and
extracting the vital sign data by obtaining objective color information from each of face images of the user taken according to the plurality of the provided camera setting values.

* * * * *